(12) United States Patent
Maschke et al.

(10) Patent No.: US 8,208,989 B2
(45) Date of Patent: Jun. 26, 2012

(54) IMPLANT, DEVICE AND METHOD FOR DETERMINING A POSITION OF THE IMPLANT IN A BODY

(75) Inventors: Michael Maschke, Lonnerstadt (DE); Ulrich Bill, Effeltrich (DE)

(73) Assignee: Siemens Akteingesellschaft, München (DE)

( * ) Notice: Subject to any disclaimer, the term of this patent is extended or adjusted under 35 U.S.C. 154(b) by 336 days.

(21) Appl. No.: 11/489,878

(22) Filed: Jul. 20, 2006

(65) Prior Publication Data

US 2007/0238984 A1    Oct. 11, 2007

(30) Foreign Application Priority Data

Jul. 21, 2005  (DE) .......................... 10 2005 034 167

(51) Int. Cl.
*A61B 5/05* (2006.01)
(52) U.S. Cl. ...... 600/424; 623/1.11; 623/1.12; 623/1.13; 623/1.14; 623/1.15; 623/1.16; 623/1.17
(58) Field of Classification Search ........ 623/1.11–1.17; 600/424
See application file for complete search history.

(56) References Cited

U.S. PATENT DOCUMENTS

| | | | |
|---|---|---|---|
| 4,654,658 A | 3/1987 | Walton | |
| 5,161,536 A | 11/1992 | Vilkomerson et al. | |
| 6,009,878 A * | 1/2000 | Weijand et al. | 128/899 |
| 6,053,873 A * | 4/2000 | Govari et al. | 600/505 |
| 6,233,476 B1 | 5/2001 | Strommer et al. | |
| 6,239,724 B1 | 5/2001 | Doron et al. | |
| 6,305,381 B1 | 10/2001 | Weijand et al. | |
| 6,488,704 B1 * | 12/2002 | Connelly et al. | 623/1.15 |
| 6,755,856 B2 | 6/2004 | Fierens et al. | |
| 2002/0107445 A1 * | 8/2002 | Govari | 600/437 |
| 2002/0147405 A1 * | 10/2002 | Denker et al. | 600/508 |
| 2003/0060702 A1 | 3/2003 | Kuth et al. | |
| 2005/0113685 A1 | 5/2005 | Maschke et al. | |

FOREIGN PATENT DOCUMENTS

| | | |
|---|---|---|
| DE | 42 15 901 A1 | 8/1993 |
| DE | 299 24 228 U1 | 8/2002 |
| DE | 101 42 253 C1 | 4/2003 |
| DE | 103 54 496 A1 | 7/2005 |
| EP | 0 885 594 B1 | 12/1998 |
| EP | 1 252 860 A1 | 10/2002 |
| EP | 1543766 A1 | 6/2005 |
| JP | 11313894 A | 11/1999 |
| JP | 2005052642 A | 3/2005 |
| WO | WO 01/05332 A1 | 1/2001 |

* cited by examiner

*Primary Examiner* — James Kish

(57) ABSTRACT

The invention relates to an implant, a method and a device for determining the position of the implant. To improve the accuracy of determining the position it is proposed to provide a transponder on the implant suitable for determining the position.

6 Claims, 4 Drawing Sheets

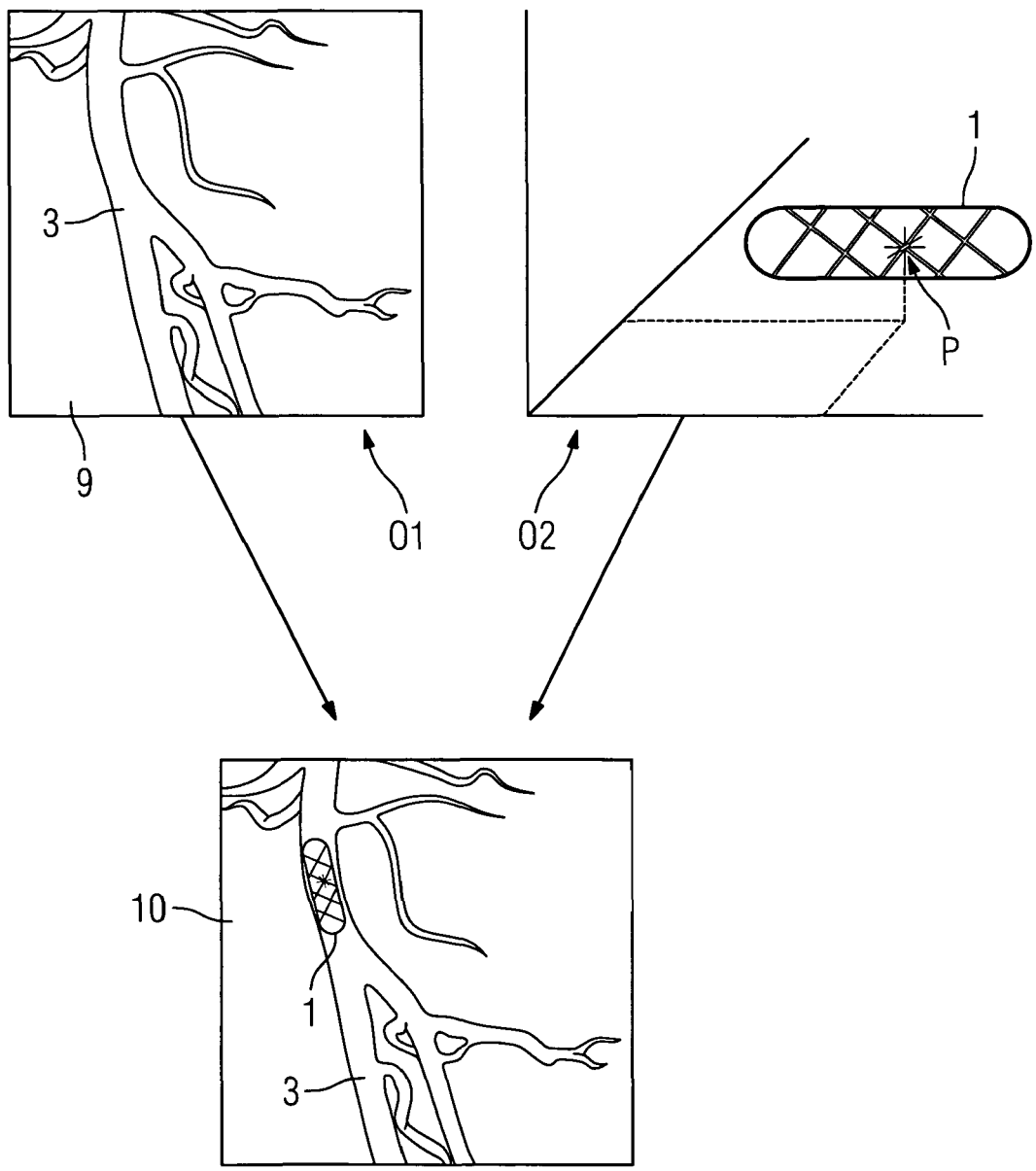

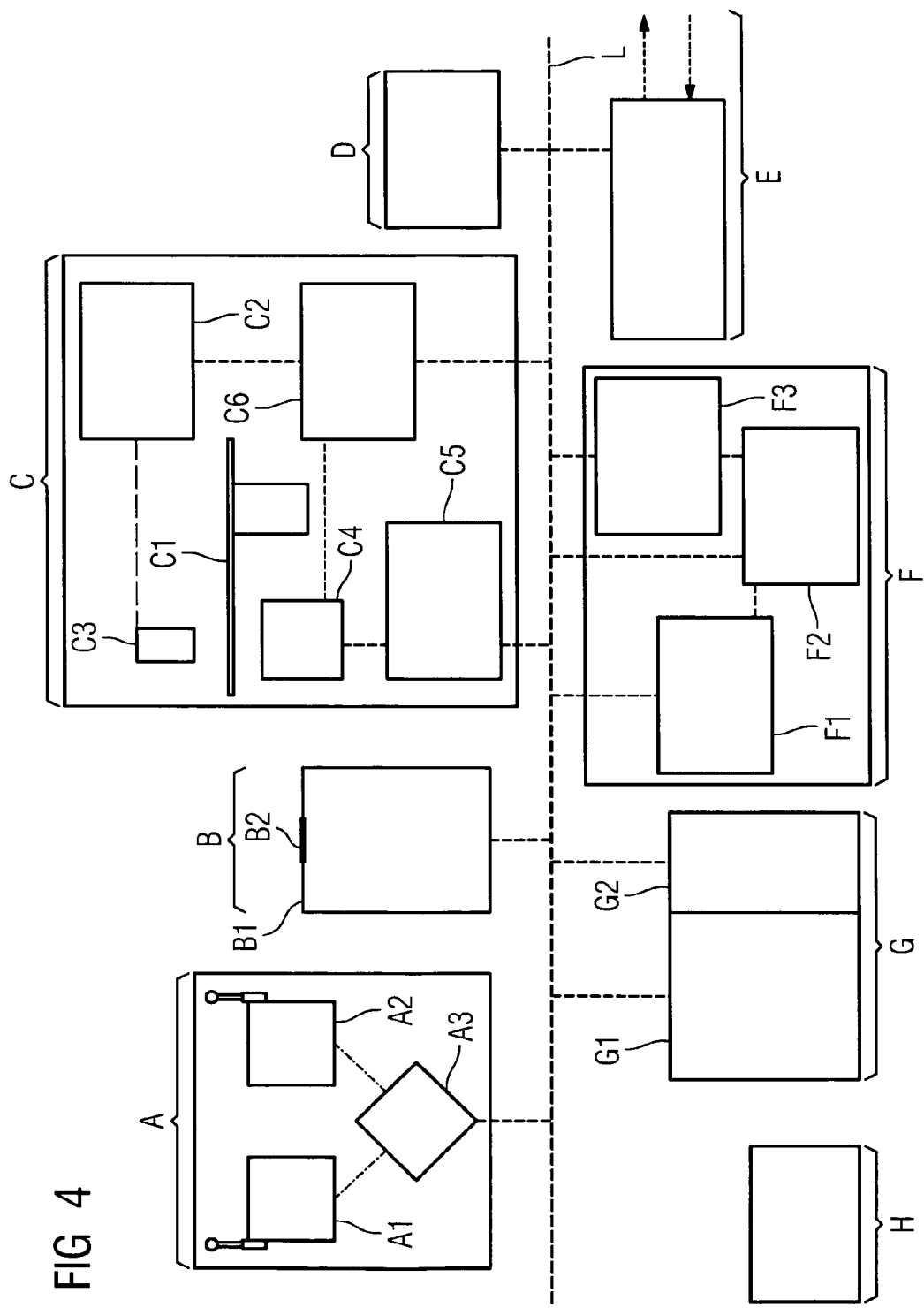

IMPLANT, DEVICE AND METHOD FOR DETERMINING A POSITION OF THE IMPLANT IN A BODY

CROSS REFERENCE TO RELATED APPLICATIONS

This application claims priority of German application No. 10 2005 034 167.5 filed Jul. 21, 2005, which is incorporated by reference herein in its entirety.

FIELD OF THE INVENTION

The invention relates to an implant as well as to a device and a method for determining a position of the implant in a body.

BACKGROUND OF THE INVENTION

An implant for insertion into the body is known from DE 299 24 228 U1. The implant concerned is a stent for prophylaxy of a restenosis of a vessel. In general stents are inserted into hollow vessels, such as blood vessels or body openings for example, in order to open these out and keep them in their expanded state. Usually catheters and guide wires are employed to insert the stent.

In coronary angiography the localization of the stent with reference to x-ray images of the body tissue is also known. Stents which are manufactured from materials with a low x-ray absorption sometimes cannot be made visible or cannot be made sufficiently visible for radiographical purposes in the body tissue.

To determine the position of the stent it is also normal to localize the catheter or guide wire with reference to x-ray markers applied to it. One disadvantage of this method is that the position of stents which cannot be localized radiographically after removal of the catheter or of the guide wire can no longer be determined.

Furthermore it is necessary to record a plurality of x-ray images for localization on introduction of the stent into the vessel. This subjects both the patient and also the medical personnel to a high dose of radiation.

An imaging method is known from EP 0 885 594 B1 in which ultrasound images can be recorded by means of a catheter to be introduced into the vessel. The ultrasound images serve as an aid for introducing and positioning the stent in the vessel. A disadvantage of this method is that the catheter used for ultrasound imaging has to be removed from the vessel before the stent is inserted. The position of the stent cannot be traced while it is being inserted.

A catheter with a localizable end area is known from DE 42 15 901. A coil is accommodated in the end area. A magnetic field can be generated with the coil. The position of the end area is determined with reference to the magnetic field distribution of the magnetic field. A disadvantage is that the measurement device used for this must be arranged in a screening chamber. Furthermore, to feed electrical energy to the coil to generate the magnetic field, the catheter must always be connected to a supply lead. This significantly restricts the handling capabilities of the catheter.

A device for determining the position of an end area of a catheter is known from U.S. Pat. No. 6,233,476 B1. Magnetic field strengths measured by Hall sensors are used to determine the position. A disadvantage of the known device is that the catheter can only be employed in few special medical applications. Furthermore the accuracy of the position determination is very badly affected by metallic objects located in the vicinity of the end area.

SUMMARY OF THE INVENTION

The object of the invention is to overcome the disadvantages of the prior art. In particular an implant, a device and also a method for determining the position of an implant in a body is to be provided, which make it possible especially easily and precisely to determine the position of the implant in the body.

This object is achieved by the features of the independent claims. Useful embodiments emerge from the features of the dependent claims.

In accordance with the present invention an implant is provided, for which, to determine the position of the implant in the body a suitable transponder is provided.

The term "suitable transponder" is taken to mean a transponder of which the co-ordinates can be determined in a co-ordinate system, based on electromagnetic radiation transmitted by the transponder and received by a receiver. The body concerned can be the body of a mammal, especially a human body. Implants able to be inserted permanently or temporarily into the body are considered to be implants. The implant can be an artificial implant. The implant can be made at least partly from inorganic materials, such as metals, plastics, ceramics etc. The implant can involve a replacement for a body tissue. It can also be an implant for supporting or taking over natural functions of tissue, organs and such like of a body of a living being.

The position of the inventive implant in the body can be determined by transmitting first electromagnetic radiation to the transponder. The transponder is excited by the first radiation. As a result of the excitation the transponder emits an electromagnetic second radiation. The second radiation can be created by modulating the first radiation. The second radiation is received by a receiver outside the body. The position of the transponder can be determined on the basis of the received radiation.

By applying transponder technology the position can be determined especially simply, accurately and reliably. A method for determining the position by means of transponders is for example known from U.S. Pat. No. 4,654,658.

The position of the implant in the body can be determined directly, independently of medical aids, such as catheters, guide wires and such like. The position of the implant can be continuously traced in a simple manner during its insertion into the body. Furthermore the position of an implant already inserted into the body can be determined subsequently without further medical intervention. A check can be made particularly quickly and easily at a later point in time as to whether the position of the implant in the body has changed.

The position of the implant can then be determined, even if the implant cannot be localized or not sufficiently localized using conventional imaging methods, such as x-ray methods for example.

Both active and passive transponders can be used as transponders. The advantage of passive transponders over active transponders is that they do not require their own energy supply. The energy required for emitting the second radiation is taken by the passive transponder from the first radiation. The passive transponder essentially makes it possible to determine the position without any time restrictions. With an active transponder on the other hand the determination of the position is restricted to the lifetime of the transponder's own power supply. An active transponder offers the advantage that it is not limited by energy taken from the first radiation. An active emission enables a greater range of the second radiation to be achieved.

In accordance with an embodiment of the invention the transponder features transmit and/or receive antennas for transmitting and/or receiving signals from at least two different directions. In accordance with the alignment of the send and/or receive antennas signals can be sent and/or received directionally. The directionality can be used to determine the position. The known alignment of the transmit and/or receive antennas relative to a transceiver unit of the transponder enables the orientation of the transponder to be determined.

A number of transponders can also be provided of which the transmit and/or receive directions are differently aligned. With direction information from a number of different directions the accuracy of the determination of the position can be increased. Provided the alignment of the transmit and/or receive directions relative to the implant or the orientation of the transponder is known, the orientation of the implant can be determined.

In accordance with an embodiment of the invention, a structural element of the implant forms a transmit and/or receive antenna of the transponder. It is only necessary to provide the transceiver unit of the transponder on the implant. This makes a particularly compact design possible. Furthermore the transmit and receive antennas can be embodied especially large. The sensitivity of the transponder and the transmit and/or receive quality can be improved. The grid-shaped basic chassis of a stent made of metal can be used as the transmit and/or receive antenna for example.

In accordance with an embodiment of the implant, the angle between the relevant longitudinal axes of two transponders lies in a range between 0° and 90°, preferably between 30° and 60°.

Preferably the angle is chosen so that an especially compact overall arrangement of the transponder is produced.

In accordance with an advantageous embodiment a longitudinal dimension of the transmit and/or receive unit of the transponder is less than 3 mm, preferably less than 1 mm. For manufacturing these types of transponder methods known from micro- and nanotechnology such as soft lithography or such like can be used for example. As a result of the small dimensions of the transponders these can be used for almost all implants. Any detrimental effect on the specified use or function of the implant can be avoided.

In accordance with an embodiment of the invention the transponder has a memory to store the position. An end position of the implant on insertion of the implant into the body can be stored in the memory. The stored position can be read out at a later time and for example compared with a new position determined. The orientation of the transponder relative to the implant can also be stored in the memory. Stored information about the position is available at all times and can be read out without any great effort. In addition to information about the position of the implant, further data, such as patient-specific data for example, can be stored.

By comparing the stored position with a position of the implant determined at a later point in time it is a simple matter to determine a change in the position or location of the implant. Regardless of the position, further data such as the date of the insertion of the implant, patient data and also a technical and medical data of the transponder and of the implant can be stored in the memory.

A sensor element to record physical and/all physiological data of the body can be incorporated into the implant. A number of sensor elements can also be incorporated. The sensor element preferably has an average size of less than 100 µm, preferably of less than 100 nm. The physical or physiological data can for example be a temperature, pressure, pH value, enzyme activity or information about molecular and/or genetic markers and such like. The data can be transmitted via the transmit antennas of the transponder to a receiver unit.

The implant can be an implant for treating heart diseases, such as a heart pacemaker, stent and such like for example. The implant can also be an implant for treating Parkinson's disease, such as a brain pacemaker for example. Further implants can be hearing prosthetics for the deaf, depots for medicines, bone implants, joint implants as well as all types of implants of plastic surgery.

In accordance with a further aspect of the invention a device for determining a position of an inventive implant equipped with a transponder in a body with a) A recording device for recording an image data set assigned to a first co-ordinate system for generating a first image of a section of the body containing at least the implant, b) A transmitter for sending an electromagnetic first radiation to the transponder, c) A receiver for receiving a second electromagnetic radiation emitted by the transponder as a result of the first radiation, d) A position determination device for determining the position of the transponder in a second co-ordinate system based on the second radiation, e) A correlation means for correlating the first and the second co-ordinate system and f) An image generation means for generating a second image which reproduces the first image and the position of the transponder.

The position of the inventive implant can be determined with the device. The position can be determined especially simply and precisely with the inventive implant. The position determination device is provided to determine the position in the second co-ordinate system. The position is determined on the basis of the second radiation emitted by the transponder and received by the receiver. The second radiation is emitted as a result of the first irradiation with the transmitter. The second radiation can for example involve a modulation of the first radiation. To receive the second radiation one or more receivers can be provided. The receiver or receivers can be accommodated on the device so that they can be moved, displaced, turned or rotated around an axis. In a similar fashion a number of transmitters can also be accommodated on the device. A second radiation emitted in different directions can be recorded particularly accurately. For determination of the position the directionality and/or dependence on distance of the second radiation can be used. The transmitters and/or receivers can be operated with different frequencies to prevent them affecting one another.

The position determined with the position determination device is presented by the image generation means together with a first image in a second image. A data set recorded with the recording device is used to generate the first image. To enable the position to be reproduced in the second image, a correlation of the first co-ordinate system assigned to the image data set with the second co-ordinate system assigned to the position is necessary. The correlation means is provided for the correlation. After successful correlation the first and the second co-ordinate system can for example the merged into one another using a co-ordinate transformation.

Phantoms can be used to determine a suitable correlation data for correlation. Markers which can be recorded by the recording device, for example x-ray markers and further transponders can be provided on the phantom. Furthermore further markers and/or further transponders can be provided on the device and the recording device. On the basis of the further markers and/or further transponders the correlation can be greatly simplified.

After correlation of the first and the second co-ordinate system the image generation means generates the second image which represents the first image and the position of the transponder contained within it.

The first image can be used as the basis for the presentation of a number of positions determined consecutively. For example the positions determined when a stent is inserted into a vessel can be presented in a single x-ray image. The positions can be represented as individual points or in the form of a trajectory. It is not necessary to record a new image data set for each new position. Because a smaller number of image data sets to be recorded is required the radiation dose of caused by an x-ray device used as recording device can typically be greatly reduced for patients and operating personnel.

In accordance with an embodiment of the device the first and/or second radiation has a first and/or second frequency of less than 100 MHz, preferably of less than 1 MHz. These types of frequency are especially well suited for an antenna size of the transponder in the range of millimeters for determining the position in an organic tissue. The first and/or second radiation can penetrate the tissue especially well. Preferably frequencies are selected which are little absorbed by the body and do not significantly adversely affect the function of medical equipment and devices.

In accordance with an embodiment of the device the first and/or second frequency alternates over time between predetermined first and/or second frequency values in each case. Frequency-dependent noise influences as well as the formation of interference resonances can be avoided. Furthermore frequency dependencies of the first and/or second radiation can be determined and used for determining the position. For example information about the distance between transponder and receiver can be determined from a different absorption, a different run time behavior of two spectral lines with different frequencies and such like.

In accordance with an embodiment of the device the transmitter can be operated with a pulsed direct current. By using a pulsed correct current noise effects caused by metal surfaces can be reduced. This enables the accuracy of the determination of the position to be improved.

In accordance with a further embodiment of the invention, one of the imaging methods selected from the following group can be used for the recording device: Sonography, radiology, fluoroscopy, fluoroscopy with optical markers, angiography, optical coherence tomography, discreet tomography, positron emission tomography, computer tomography, nuclear resonance tomography, endoscopy, nuclear medical imaging methods, optical imaging methods. A combination of two or more imaging methods can also be used. A one, two-, three- or four-dimensional image data set can be recorded as required. Parameter values of the recording device used in the recording of the image data set a can be used by the image generation means for generating the second image.

In accordance with a further embodiment the body is a mammalian body, especially a human body and furthermore a catheter for insertion into a vessel, a tube and/or a hollow space of the body is provided on the device. On the basis of the catheter for example internal images of the vessel, the tube and such like can be generated with an imaging ultrasound device fitted to it. These images can be used for the generation of the second image.

In accordance with an embodiment of the device at least one further transponder is provided on the device and/or on the catheter. The further transponder is preferably fixed to the device, preferably at a tip of the catheter. On the basis of the further transponder or transponders additional information for determining the position, e.g. direction or distance information can be obtained. Correlation data for correlation of the first and second co-ordinate system can also be determined.

In accordance with a further embodiment of the device, a device is provided for recording a movement of the body. The device can be used to record external and/or internal movements. The movements recorded with the device can be used to correct movement artifacts in the first image, in the second image and/or for the determination of the position. To record the movement the device can comprise a camera, a laser, magnetic sensors, pressure sensors, and electrocardiograph and/or a blood pressure sensor. A camera and/or a laser are particularly well suited to recording external movements of the body. Electrocardiographic data as well as blood pressure data are especially well suited for recording internal movements which are caused by the heartbeat. Magnetic sensors or pressure sensors can be used for example to record a movement caused by the breathing of a patient.

In accordance with an embodiment of the device an interface is provided for wireless transmission of data from and to the device and/or between components of the device. The data concerned can be position data, image data, physiological data, patient data and such like. The data can be transmitted from and to a computer connected to a network, e.g. within a hospital information system. A wireless transmission of data between the components of the device can be undertaken for example between the transmitter, the receiver and the position determining device, between the recording device and the image generation device, between the correlation means and the image generation means, between the catheter and the position determining device etc.

In accordance with an embodiment of the device the position determining unit determines a plurality of different positions for a movement of the transponder and/or of the further transponder in a hollow, pipe-shaped or tubular area of the body. The area of the body can for example be a section of a vessel. The determining of the plurality of positions can be viewed as the point-by-point scanning of the volume of the area. The positions can be used by an envelope curve determining unit for determining an envelope curve enclosing the volume. The envelope curve can be presented in the second image.

In accordance with an embodiment of the device a suitable phantom is provided for determining correlation data for correlating the first and second co-ordinate system. With the additional correlation data determined using the phantom the correlation can be simplified and improved.

In accordance with an embodiment of the invention, the transponder, the further transponders, sensors, cables, electronic components and/or housings feature screening against electromagnetic interference fields. Adverse effects on the functioning of the device caused by electromagnetic interference fields can be reduced.

In accordance with a further embodiment of the invention a power network provided for operating the device is electrically separated from an electrically-conductive element of the device connected to the body. The electrically-conductive element can for example be a metal surface, sensors for recording physiological data connected to the device such as for example electrocardiography electrodes etc. It can be ensured that if there is a defect neither the patient nor the operating personnel of the device are endangered.

In accordance with a further advantageous embodiment of the invention a DICOM, protocol interface is provided for exchange of data, especially-image data. Preferably the DICOM protocol interface includes an MPPS (Modality Performed Procedure Step) module. The interface and the module involved are standardized interfaces which can be used for medical image data. The interfaces allow a simple exchange of image data with other DICOM-enabled medical devices. The MPPS module allows a standardized and especially simple processing of image information.

In accordance with another aspect of invention a method is provided for determining the position of an inventive implant equipped with a transponder in a body, with the following steps:
a) Recording an image data set assigned to a first co-ordinate system for generating a first image of a section of the body containing at least the implant,
b) Transmitting an electromagnetic first radiation to the transponder,
c) Receiving a second electromagnetic radiation emitted by the transponder as a result of the first radiation,
d) Determining the position of the transponder in a second co-ordinate system based on the second radiation,
e) Correlating the first and the second co-ordinate system and
f) Generating a second image which reproduces the first image and the position of the transponder.

With reference to the advantageous embodiments of the method the reader is referred to the advantageous embodiments of the device described above.

The inventive implant, the device and also the method allow an especially simple and precise determination of the position of the implant in the body. The use of transponder technology enables the determination of the position to be essentially independent of the imaging method. In particular it is not necessary for the implant to be able to be localized with the imaging method employed at the time.

BRIEF DESCRIPTION OF THE DRAWINGS

The invention is explained in greater detail below with reference to advantageous exemplary embodiments. The figures show.

Unless otherwise stated the same reference symbols in FIG. 1 to 4 designate the same or similar elements.

DETAILED DESCRIPTION OF THE INVENTION

Figure 1:
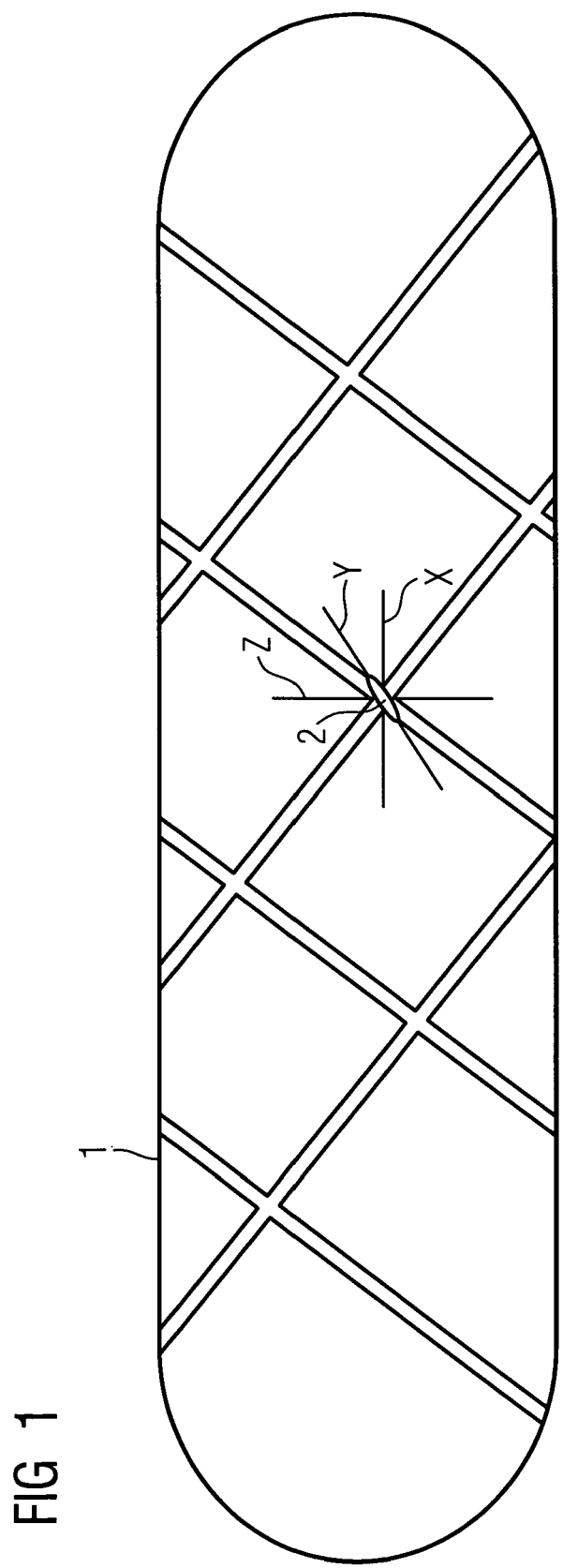
FIG. 1 a stent,
FIG. 2 a schematic diagram of an arrangement for determining the position of the stent in FIG. 1,
FIG. 3 a schematic diagram of a correlation process and
FIG. 4 a block diagram of a device for determining a position of an implant equipped with a transponder.

FIG. 1 shows a stent 1 with a transponder 2 fitted to it, X, Y, Z, indicate an X-, Y- and Z direction of transmit and/or receive antennas of the transponder 2 not shown in the diagram.

The stent 1 is embodied in the form of a tubular mesh. The mesh is constructed from a base material, such as stainless steel, Lithinol or other materials usual for stents 1. The mesh can be provided with a coating. The coating can be intended to protect the mesh and/or have a suitable substance for preventing restenoses of a vessel. The transponder 2 is fitted to the mesh of the stent 1. The transponder 2 features transmit and/or receive antennas not shown in the diagram for transmitting and/or receiving signals to/from of the X-, Y- and Z directions at right angles to each other. There can essentially be any number of transmit or receive directions. For example the Y direction can represent a receive direction and the X direction as well as the Z direction a transmit direction. The transponder 2 can also feature more or less than 3 transmit and/or receive directions. Thus a number of transponders each with one or more differently aligned transmit and/or receive directions can be provided.

The size of the transponder 2 preferably lies in the range of a few millimeters, preferably in the sub-millimeter range. A length dimension of the transmit and/or receive units of the transponder 2 is in this case less than 3 mm or 1 mm.

The transponder 2 concerned can be a passive or an active transponder 2. The passive transponder 2 offers the advantage that the energy consumed by the transponder 2 is supplied from outside via an electromagnetic field. The passive transponder 2 does not need its own energy supply, such as a battery for example. The active transponder 2 on the other hand needs a separate energy supply. The period during which the active transponder can be used is limited to the lifetime of the energy supply. With active transponders 2 however a greater signal strength of the signal transmitted by the unit and a greater range can be achieved.

The transponder 2 can also have a memory. The position of the transponder 2 in the body and the orientation of the transponder 2 relative to the stent 1 can be stored in the memory. Further data, such as patient data, information about the stent 1, such as material and coating for example, can be stored in the memory.

A sensor element to record physical and/or physiological data of the body can be incorporated into the stent 1. The sensor element can be used for example for recording temperature, pressure, pH-value. A sensor element to record a genetic and/or molecular variable can be provided. The variable involved can for example be information about enzyme activity, genetic and/or molecular markers. The data recorded by means of the sensor element can be stored or buffered in the memory of the transponder. The receive antennas of the transponder can be used for transmitting the data to a receiver unit. The sensor element is preferably smaller than the length dimension. The sensor element can have an average size of less than 100 µm, preferably of less than 100 nm.

Figure 2:
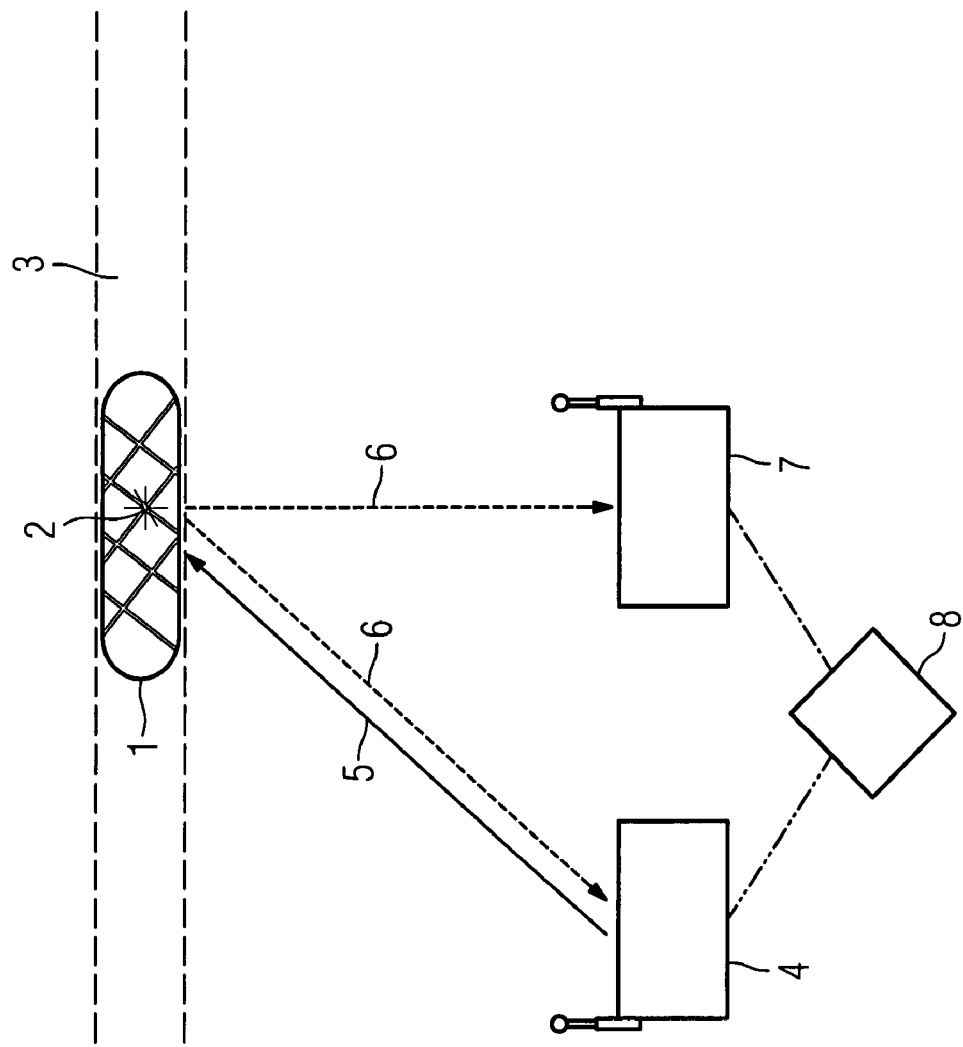

FIG. 2 shows schematically an arrangement for determining the position of the stent 1 of FIG. 1. The stent 1 and the transponder 2 provided on it is used for prophylaxy of a restenosis in a vessel 3. For determining the position of the implant a transceiver 4 with a transmitter for transmitting an electromagnetic first radiation 5 to the transponder 2 and a receiver for receiving a second electromagnetic radiation 6 emitted by the transponder as a result of the first radiation 6 is provided. A receiver 7 is provided for recording a property the second radiation 6 depending on the distance to the transponder 2. The reference symbol 8 indicates a position determination unit for determining the position of the stent 1 on the basis of the second radiation 6 received by the transceiver 4 and by the receiver 7.

The position is determined as follows:
The transceiver 4 sends the first radiation 5 to the transponder 2. The first radiation 5 activates the transponder 2. As a result of the activation the transponder 2 emits the second radiation 6. For reasons of clarity the first irradiation 5 an also the emission of the second radiation 6 in FIG. 2 are restricted to the Z- and Y-direction. The irradiation or radiation emission can be undertaken in any direction. To this end further fixed or movable transceivers and/or receivers or transmitters can be provided. For the directionality of the emitted second radiation 6 the position determination unit 8 determines direction or location information. Furthermore the position determination unit 8 determines on the basis of the second radiation 6 received from the receiver a distance of the receiver 7 from the transponder 2 in relation to the Z direction.

The receiver 7 can for example determine the magnetic field strength of the received second radiation 6 by means of a Hall sensor. Distance information can also be determined from a frequency difference between two spectral lines of the second radiation 6. To increase the accuracy of the determination of the position, location, direction and distance information can be determined for a number of different arrangements of the transceiver 4 and of the receiver 7 relative to the transponder 2. On the basis of the direction, location and distance information, the position determining unit determines the position in a second co-ordinate system. The second co-ordinate system can for example be a co-ordinate system assigned to the transceiver 4, the receiver 7 and such like. Cartesian co-ordinates, polar or cylinder co-ordinates or spherical polar co-ordinates can be used as co-ordinates of the second co-ordinate system.

With a known orientation of the transponder 2 relative to the stent 1 the position and orientation of the stent 1 can be determined. The orientation of transponder 2 can be stored in the memory of the transponder 2 stored can be read out by means of the transceiver 4 or the receiver 7. The position determining unit 8 can, on the basis of the orientation and the position of the transponder 2, determine the orientation, the precise position of the stent 1.

FIG. 3 is a schematic diagram of a correlation process. In the correlation process a first co-ordinate system O1 assigned to an x-ray image 9, is correlated with a second co-ordinate system O2. A position P of the transponder 2 or stent 1 determined by the position determination unit is shown in the second co-ordinate system O2. The reference symbol 10 indicates an overlay image generated after the correlation. The overlay image 10 contains the x-ray image 9 and reproduces the position P of the transponder 2 or stent 1.

Further transponders and/or x-ray markers can be used for the correlation of the first and second co-ordinate system. The further transponders can be mounted on the device. The x-ray markers can be accommodated in the recording area of the x-ray device. Advantageously a further transponder is provided on the x-ray marker. The positions of the further transponders and the position of the radiographically recorded x-ray markers are used to determine correlation data.

Correlation data can also be obtained on the basis of a catheter able to be inserted into the vessel not shown in the diagram. To this end one or more x-ray markers or further transponders can be provided on the catheter.

A correlation specification can be determined on the basis of the correlation data, e.g. in the form of a co-ordinate transformation for transforming the second co-ordinate system O2 into the first co-ordinate system O1. After correlation is completed the overlay image 10 is created and displayed. Information about the correlation specification and the underlying x-ray image 9 can be stored on the transponder 2.

When the stent 1 moves, e.g. on insertion of the stent 1 into the vessel 3, an ongoing series of positions P can be determined. The relevant positions P can be shown in the overlay image as a trajectory. It is also possible to only show the current position of the stent 1. To display the position P the same x-ray image 9 can be used as the basis, provided the stent does not leave the area of the body not recorded by the x-ray image 9. It is not necessary to record a plurality of x-ray images 9. The radiation dose for a patient and for the medical personnel can be significantly reduced. Furthermore less strain is imposed on the recording devices used for imaging. This leads to lower costs for recording as well as for repair and maintenance.

FIG. 4 shows a block diagram of a device for determining a position of an implant provided with a transponder.

The device features a position determination block A, a patient monitoring block B, an image recording block C, a memory block D, an interface block E, an image generation block F, an input/output block G and a power supply block H.

The position determination block A features a transceiver A1 for transmitting the electromagnetic first radiation 5 as well as for receiving the electromagnetic second radiation 6 to or from a transponder provided on an implant. Furthermore there is a receiver A2 for recording a physical variable of the second radiation 6 depending on the distance of the receiver A2 from the implant. For determining the position of the transponder in a second co-ordinate system a processor A3 is provided in the position determination block A. The processor A3 is connected for data exchange to the transceiver A1 and the receiver A2. The data can be exchanged via a cable or wirelessly, e.g. via a radio connection. The patient monitoring block B features a signal processing unit B1 for physiological data as well as terminals B2 for sensors for recording the physiological data. The signal processing unit can be used for editing or processing data which is recorded by means of a sensor element fitted to be implant for recording physical and/or physiological data. The image recording block C comprises components of an x-ray device, e.g. a C-arm x-ray device or an X-ray device or an x-ray computer tomograph. The x-ray device features a patient table C1, an X-ray emitter C3 connected to a high voltage generator C2 for generating X-ray radiation, and x-ray detector C4 for detecting the x-ray radiation and a data processing unit C5 connected to it for exchanging data. A system controller C6 is provided for controlling the components of the x-ray device. The image generation block F features a calibration unit F1 for calibrating a first and a second co-ordinate system. An image correction unit F2 is provided for correcting image artifacts. An image generation unit for creating an overlay image is indicated by the reference symbol F3. The input/output block G features a display unit G1 for displaying information, images, operating states of the blocks A to H etc. Furthermore the input/output block G features an operating unit G2. An energy supply block H is provided to supply power to the device and blocks A to H. For exchange of data and/or energy between blocks A to H or between parts thereof, these blocks are interconnected by a bus line L.

The functions of the device and the interoperation of the blocks A to H are described below.

The position of a transponder provided on an implant is determined by means of the position determining block A in a similar way to the information given for FIG. 2. The implant concerned, as well as being a stent as shown in FIG. 2 can also be a heart pacemaker, brain pacemaker, depots for medicaments which can be inserted into a body, plastic surgery implants, such as material for bone replacement.

On the basis of the patient monitoring block B, physiological data of a patient can be recorded with the signal processing unit B1. Terminals B2 for an electrocardiograph, a pulse meter, a blood pressure meter can be provided on the signal processing unit B1. Furthermore a terminal B2 for connecting a device for recording the breathing and an associated movement of the body, especially of the upper body of the patient, can be provided. On the basis of the physiological data it is possible on the one hand to monitor the state of a patient during an examination. On the other hand the physiological data, such as heartbeat, pulse or breathing for example, can be used for correcting movement-induced artifacts in the first and/or second image. Movement-induced errors in the determination of the position of the transponder can also be corrected.

An image data set for generating a first image is created with the x-ray device image recording block C. The image data set covers a section of the body of a patient accommodated on the patient table C1. The image data set concerned can be a two-dimensional, three-dimensional or four-dimensional data set. The image data set can be supplemented with further image data of other imaging systems, e.g. a catheter with ultrasound imaging or imaging by means of Optical Coherence Tomography (OCT). An x-ray image is created from the image data set by means of the data processing unit C5. A number of images of a sequence of two- or three dimensional x-ray images can also be generated.

The x-ray images generated are used by the image generation unit F3 for generating the second image. It is also possible for the image generation unit to process the image data set and the further image data directly. To calibrate the first co-ordinate system assigned to the x-ray image and the second co-ordinate system assigned to the position of the transponder a calibration is undertaken by means of the calibration unit F1. After calibration of the first and second co-ordinate system a second image is generated by the image generation unit F3. The second image reproduces the x-ray image and the position of the transponder in the body shown within it. Furthermore, provided the orientation of the transponder is known relative to the implant, the position and orientation of the implant in the body is determined and displayed by the image generation unit F3 in the second image. The orientation of the transponder relative to the implant can be obtained for example either from a data sheet of a patient file or from the orientation information stored in a memory of the transponder.

To improve the quality of the second image the physiological data recorded by the patient monitoring block B can be evaluated by the image correction unit F2 and a correction can be performed. Based on the physiological data such as breathing, heartbeat etc movement artifacts can be corrected. Movements can be recorded using a camera or by means of a laser and used for correcting the movement artifacts.

The second image generated by the image generation block F is displayed on the display unit G1 of the input/output block G. The display unit G1 concerned can for example be a monitor which is connected to a computer for controlling the x-ray device. The display unit G1 can also feature a special patient monitor provided for the display of patient-specific data. Further data such as physiological data or operating data of the x-ray device can be displayed for example on the display unit as well as the x-ray image. For the controlling, operating and/or initiating functions as well as for communication by a user with the device or with individual blocks A to H an operating unit G2 is provided in the input/output block G. The operating unit G concerned can be a computer connected to the device and the blocks A to H via a bus line L. It can also be a portable or mobile operating element, a touch-sensitive monitor or such like for example.

The x-ray image, the second image, the position of the transponder and/or the relative orientation of the transponder to the implant, patient data, recording parameters of the x-ray device and further data can be stored in the memory block D.

For exchange of medical data, especially of image data, between the device and further medical or non-medical devices a standardized interface is provided in interface block E. The interface concerned can for example be a DICOM protocol interface (DICOM, Digital Imaging and Communications in Medicine). The DICOM protocol interface can comprise an MPPS module and further modules specifically suitable for exchanging medical image data.

For exchange of data between blocks A to H or between individual components of the blocks these blocks are interconnected by a bus line L. A connection via a common bus line L is not mandatory. Individual connections can be embodied as radio connections or wireless connections. The latter are especially suitable for data transfer between a processor A3 and the transceiver A1 or the receiver A2, a well as for transmission of physiological data from the sensors to the signal processing unit B1.

With the inventive implant, the device as well as the method for determining a position of an implant provided with a transponder in a body, the position of the transponder as well as the position of the implant can be determined especially simply, precisely and reliably.

The invention claimed is:

1. An implant system including an implant for insertion into a body of a medical patient, the system providing a determination of implant position within the body, comprising:
   a transmit or receive unit, attached to the implant, including (i) a transponder to receive a first radiation signal when the implant is positioned within the body and to generate, in response to the first signal, a second radiation signal suitable for determining a position of the implant within the body, (ii) an antenna configured to transmit the second signal from the transponder to outside of the body and to receive the first signal from outside the body for transmission to the transponder, said antenna configured by a structural element of the implant to transmit the second signal in a plurality of directions, (iii) a memory unit for storing the position of the implant, and (iv) a sensor element for recording in the memory unit physical or physiological data of the body;
   a transmitter for generating and transmitting the first signal from outside the body to the transmit or receive unit when the implant is positioned within the body;
   at least one receiver for receiving the second signal at a position outside the body; and
   a position determination device operatively configured to receive (i) data associated with an image containing the implant and (ii) data based on the second signal, and to determine the position of the transponder based on correlation of the data descriptive of the image containing the implant positioned in the body with the data based on the second signal and provided from the receiver.

2. The system of claim 1, wherein the transmitter is a transceiver configured to also receive the second signal so that the position of the transponder can be determined based on the second signal received by both the receiver and the transceiver.

3. The system of claim 1, wherein a plurality of transponders each with differently aligned transmit or receive directions are provided and an angle between two longitudinal axes of two transponders is in a range of 0° to 90°.

4. The system of claim 3, wherein the angle between the two longitudinal axes of two transponders is in a range of 30° to 60°.

5. The system of claim 1, wherein the implant is a stent.

6. The implant system of claim 1 wherein the first radiation signal and the second radiation signal are each electromagnetic radiation signals.

* * * * *